US00PP16575P3

(12) United States Plant Patent
Clough

(10) Patent No.: US PP16,575 P3
(45) Date of Patent: May 30, 2006

(54) PECAN TREE 'EXCEL' VARIETY

(50) Latin Name: *Carya illinoinensis*
Varietal Denomination: EXCEL

(76) Inventor: Andy Clough, 3417 Highway 84 West, Blackshear, GA (US) 31516

( * ) Notice: Subject to any disclaimer, the term of this patent is extended or adjusted under 35 U.S.C. 154(b) by 41 days.

(21) Appl. No.: 10/806,673

(22) Filed: Mar. 23, 2004

(65) Prior Publication Data

US 2005/0216982 P1 Sep. 29, 2005

(51) Int. Cl.
*A01H 5/00* (2006.01)

(52) U.S. Cl. ..... Plt./153
(58) Field of Classification Search ..... Plt./153
See application file for complete search history.

*Primary Examiner*—Anne Marie Grunberg
*Assistant Examiner*—June Hwu
(74) *Attorney, Agent, or Firm*—Stockwell & Associates

(57) ABSTRACT

The new variety "EXCEL" pecan tree is an early bearing tree with fruit maturing and ready for harvest about the 1st week in October. The new "EXCEL" tree actually blooms out later than the popular "Stuart" variety yet this new variety actually produces mature nuts that ripen earlier. The tree displays a semi-dwarf type growth with small twiglets, yet the nut has the general size and shape of the "Desirable" pecan variety. The fruit has a thick shell and an excellent quality that yields about 51%. The final bloom is red and the catkins are long and thin. The tree has also shown to be disease resistant as well as insect resistant for the foliage. The foliage is somewhat sparse, which allows for better sunlight penetration and air circulation. On the worst of conditions, the "EXCEL" has shown no scab on the nuts. The tree is precocious (early bearing) as well as prolyfic (heavy bearing).

7 Drawing Sheets

FIELD OF THE INVENTION

This invention relates generally to a new and distinct variety of pecan tree.

Latin name of genus and species: *Carya illinoinensis* (Wangenh.) K. Koch VARIETY DENOMINATION 'EXCEL'.

Variety denomination: 'EXCEL'.

BACKGROUND OF THE INVENTION

The present invention relates to a new and distinct variety of pecan tree discovered growing by the inventor on his farm in Pierce County, Ga. The instant tree is selected from seedlings of unknown parentage and will be known commercially as the 'EXCEL' variety and known scientifically as *Carya illinoinensis*.

BRIEF SUMMARY OF THE INVENTION

The tree of the new 'EXCEL' variety was found growing in a planted orchard on the inventor's farm in the year of 1990. The tree was estimated to be between about 20 and 25 years old at the time of discovery. The inventor's attention was attracted to the original tree of the new 'EXCEL' variety because of its superior characteristics.

In particular, the new variety 'EXCEL' pecan tree is an early bearing tree with fruit maturing and ready for harvest about the 1st week in October, which puts this new variety at about 2 weeks earlier than the standard 'Stuart' variety. Surprisingly, the new 'EXCEL' tree actually blooms out later than the popular 'Stuart' variety yet this new variety actually produces mature nuts that ripen earlier.

The new 'EXCEL' tree displays a semi-dwarf type growth with small twiglets, yet the nut has the general size and shape of the 'Desirable' pecan variety. The fruit has a thick shell and an excellent quality that yields about 51%. The final bloom is red and the catkins are long and thin. At this time the new variety is thought to be a self-pollinator.

The 'EXCEL' tree has also shown to be disease resistant as well as insect resistant for the foliage. The foliage of this new variety is somewhat sparse, which allows for better sunlight penetration and air circulation. On the worst of conditions, the 'EXCEL' tree has shown no scab on the nuts. The tree is precocious (early bearing) as well as prolific (heavy bearing).

Trees of the new 'EXCEL' variety have been asexually reproduced by grafting and budding by the inventor at his farm in Pierce County Georgia. Asexual reproduction has shown that the foregoing characteristics and distinctions survive and are established and transmitted through successive propagations as witnessed by University of Georgia Plant Pathologist, Dr. Patrick Conner, or Athens, Ga.

BRIEF DESCRIPTION OF THE PHOTOGRAPHS

The photographs show various aspects of the new 'EXCEL' variety while being grown at Pierce County near Blackshear, Ga., wherein the color is illustrated as true as is reasonably possible in a depiction of this character.

DETAILED DESCRIPTION OF THE PREFERRED EMBODIMENTS

Figure 1:
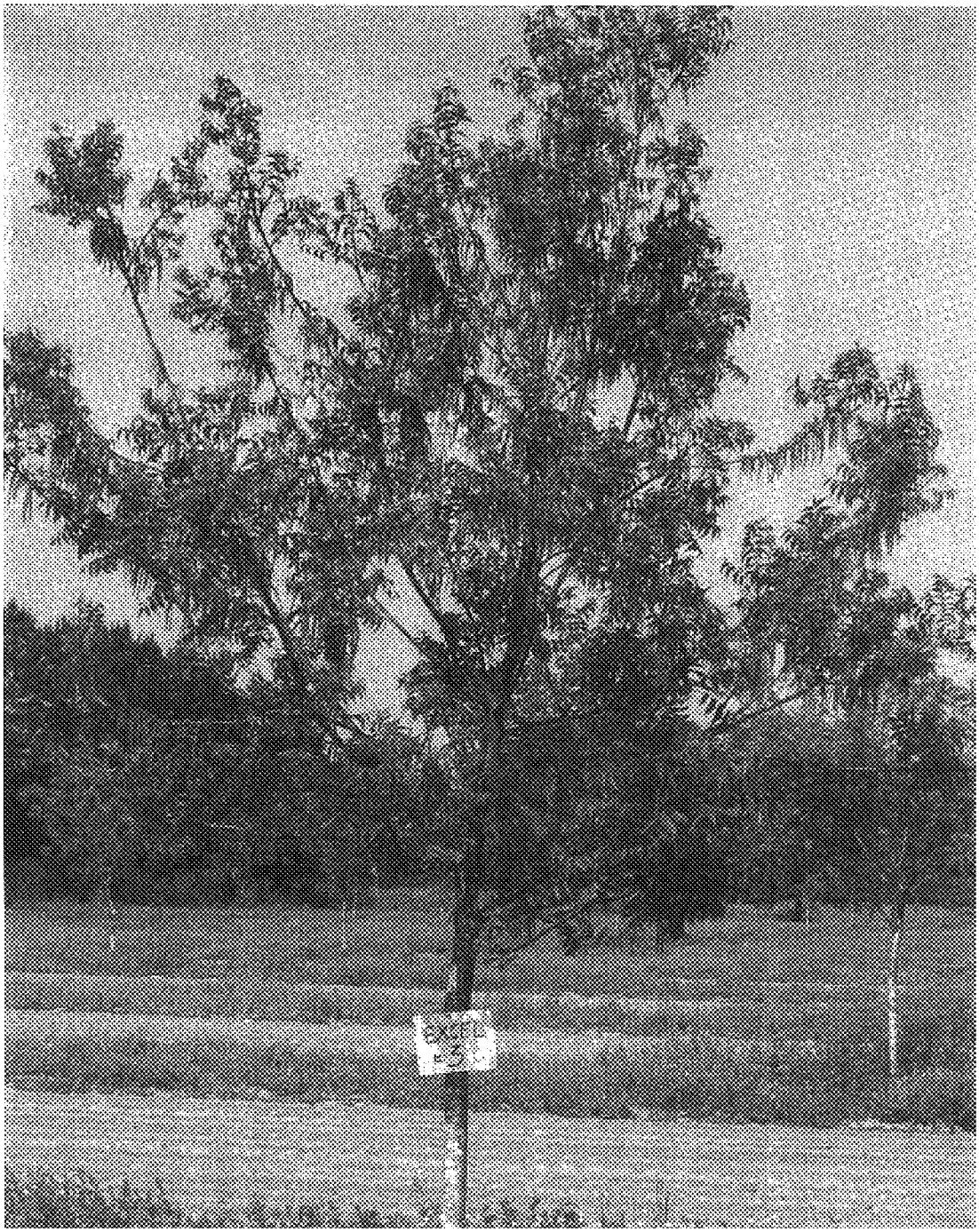
FIG. 1 shows the generally upright and spreading sturdy growth habit of the original tree of the new 'EXCEL' variety when observed in 2001.

Having summarized various aspects of the present invention, reference will now be made in detail to the description of the invention as illustrated in the accompanying photographs.

The tree:

*Tree configuration.*—Sparse, open tube growth showing small leaves and twig bits or semi dwarf and conducive to closer planting, displays a semi-dwarf type growth with small twiglets, foliage is somewhat sparse, which allows for better sunlight penetration and air circulation Tree has good strong branch junctions.

*Foliage.*—Foliage displays somewhat small leaflets which are of medium green color.

*Productivity.*—Bearing age approximately 3 years, good regular bearer of quality nuts; trees have been shown to bear at 3 years after transplanting and shown increased heavy production, thereafter.

*Buds.*—Buds are spaced somewhat far apart on twiglets, long & pointed.

*Catkins.*—The final bloom is red and the catkins are long and thin. Female bloom is red, catkins are somewhat light in color.

*Hardiness.*—Tree blooms late and matures early leaving it less susceptible to frost damage.

*Resistance to disease and insects.*—Nuts have shown high resistance to scab and other disease; foliage has shown heavy resistance to disease as well as good resistance to insects.

The nuts:

*Ripening.*—Early bearing tree with fruit ready to shake about the 1$^{st}$ week in October, which puts it about 2 weeks earlier than the standard Stuart variety. The last picking date would then be around October 15. The 'EXCEL' tree of the present invention thus actually blooms out later than the 'Stuart' variety but matures earlier. Pecan fruit are covered by a thin 4-valved husk referred to as the "schuck". Thus, the term "schuck split" refers to the date when approximately ½ the nuts have sutures that have split to the husk base. This exposes the shell of the nut, which then often hangs with the drying husk for several weeks. The date of "schuck split" is a common method of determining average harvest date of pecan varieties, which is an important variable among pecan cultivars. Accordingly, for the 'EXCEL' variety of the present invention, Schuck split begins around September 20$^{th}$, and nuts open uniformly a few days afterward.

*Maturity.*—Nuts are ready to shake the 1$^{st}$ week in October.

*Quantity.*—Nut count is about 45 per pound.

*Nuts per cluster.*—Generally 3 to 5.

*Configuration.*—Nuts are in a tight cluster and shaped similar to a desirable variety.

*Shell.*—Thick showing good bird resistance and adaptable to machine harvest.

*Kernel.*—Excellent, bright meat, heavy oil content, yields about 51% with very consistent quality.

*Weight.*—Some 7 year old trees have produced 50 pound or more.

*Size.*—45 cm. Nuts are larger and consistent with the general size and appearance of desirable variety.

The following are color descriptions of the present invention, referencing The R.H.S. Colour Chart.

Bark: RHS N200C.
Foliage upper: RHS 146A.
Foliage lower: RHS 146B.
Leaf venation: RHS 145C.
Branch: RHS 199A.
Lenticels: RHS 167D.
Petiole: RHS 144B.
Winter leaf buds: RHS N199B.
Male catkins: RHS 143C.
Female inflorescence: RHS 141C.
Husk: RHS 137A.
Nut: RHS 200C.
Kernel: RHS 164B.

Figure 2:
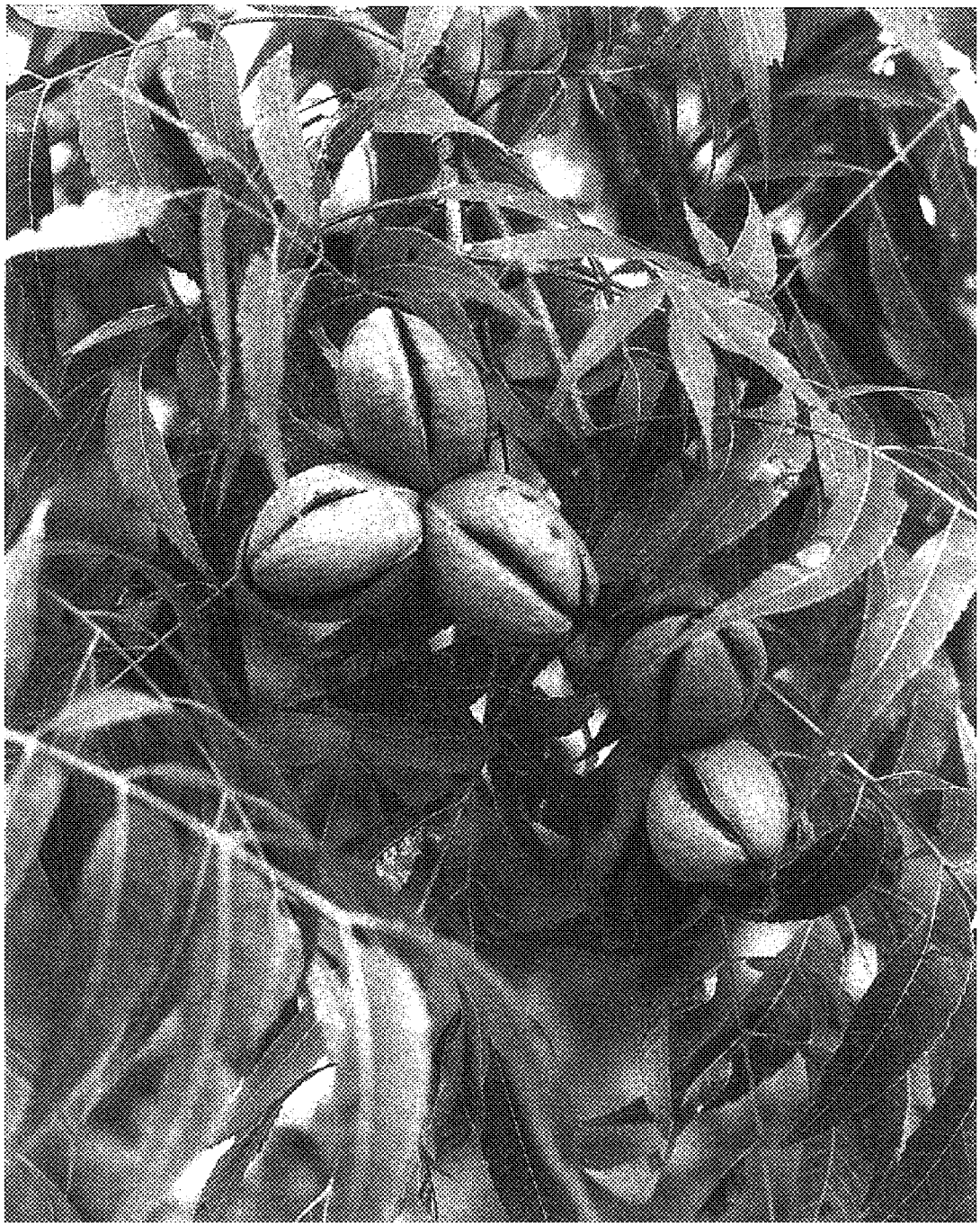
FIG. 2 shows typical foliage and nuts of the new 'EXCEL' variety during spring, summer, and fall of 2002.
Figure 3:
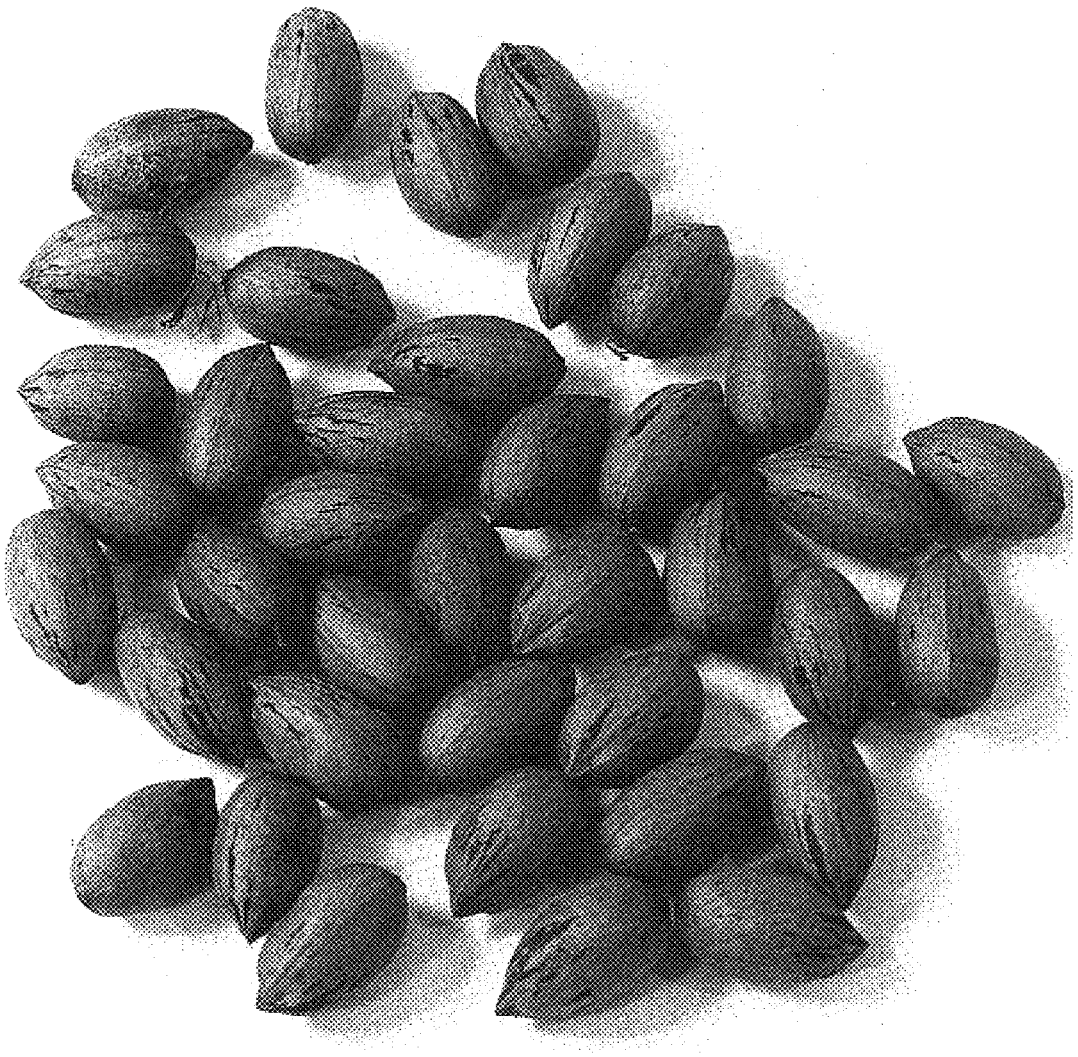
FIG. 3 illustrates typical nuts of the new 'EXCEL' variety following removal from the husks.
Figure 4:
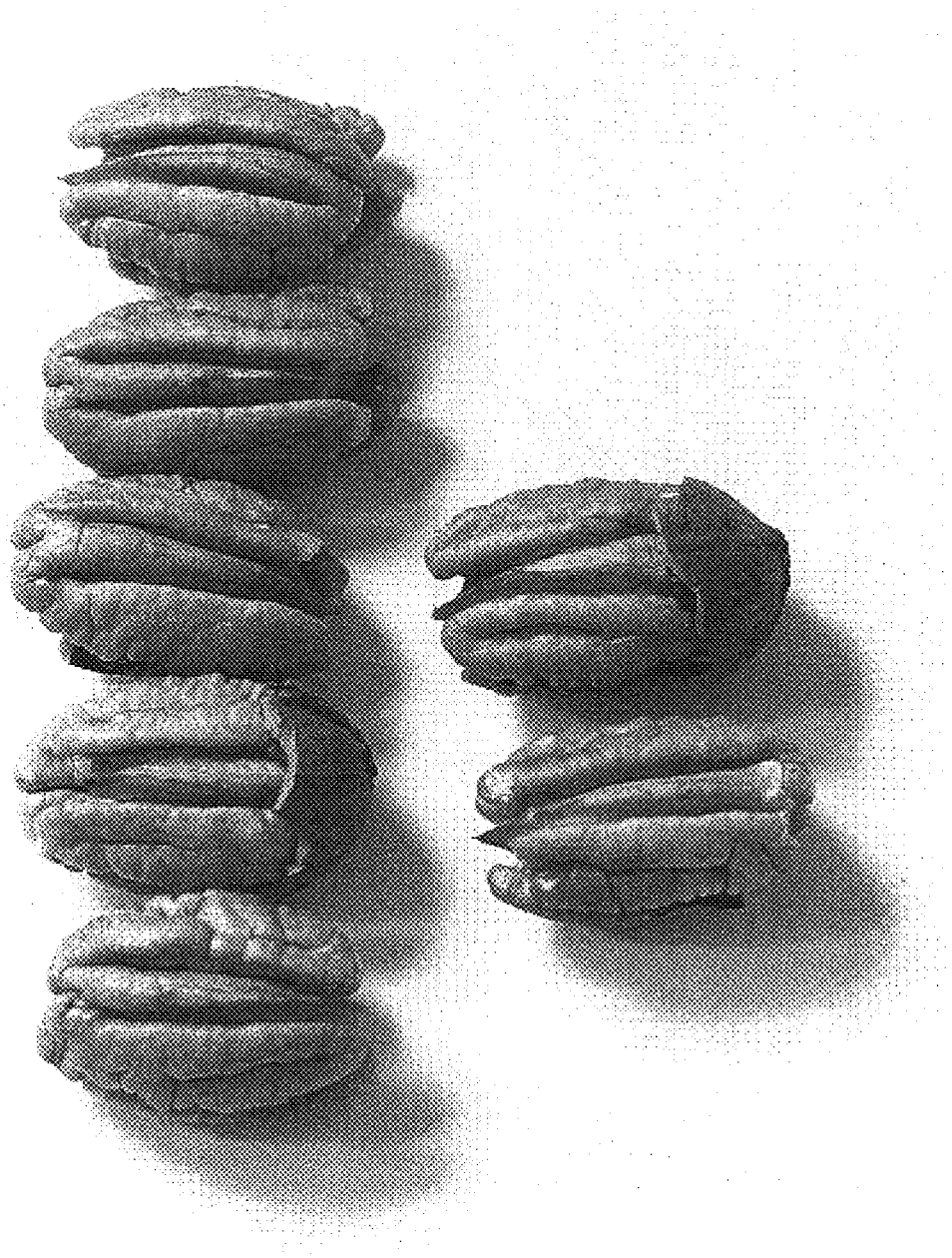
FIG. 4 illustrates typical nuts of the new 'EXCEL' variety showing the kernels following removal from the shell.
Figure 5:
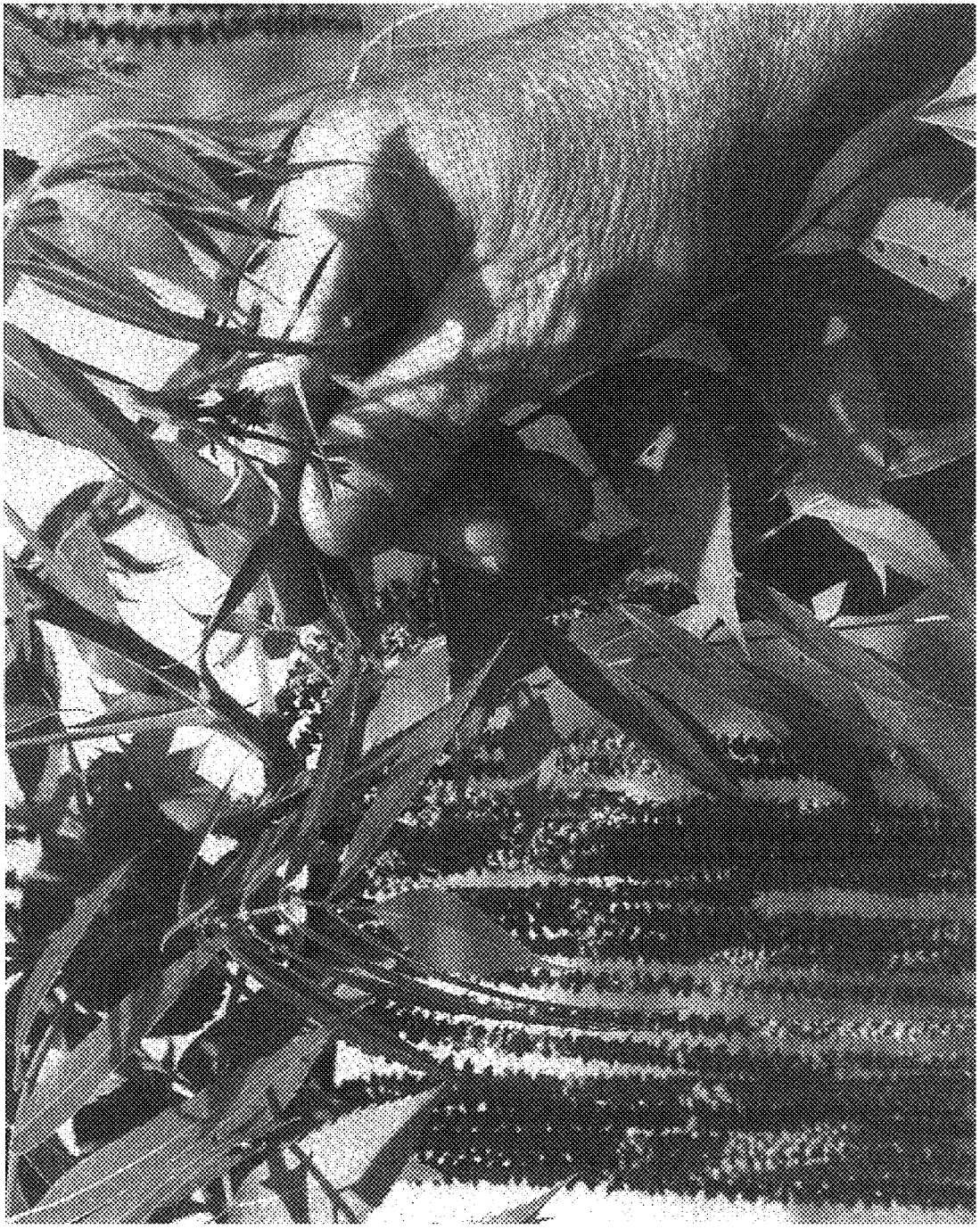
FIG. 5 illustrates typical foliage, buds, and catkins of the new 'EXCEL' when the tree is in bloom.
Figure 6:
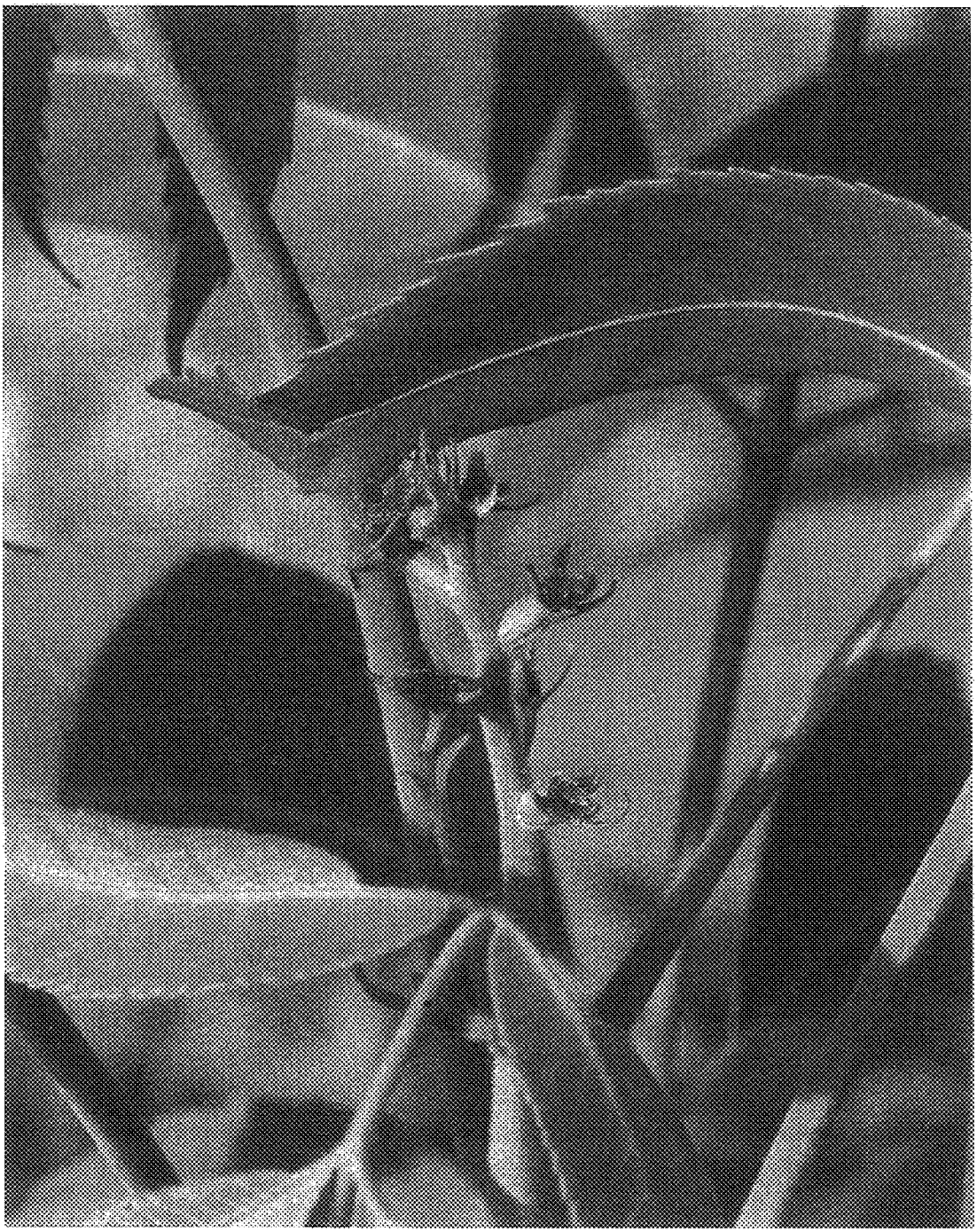
FIG. 6 is a close up picture illustrating the typical bloom of the new 'EXCEL' variety.
Figure 7:
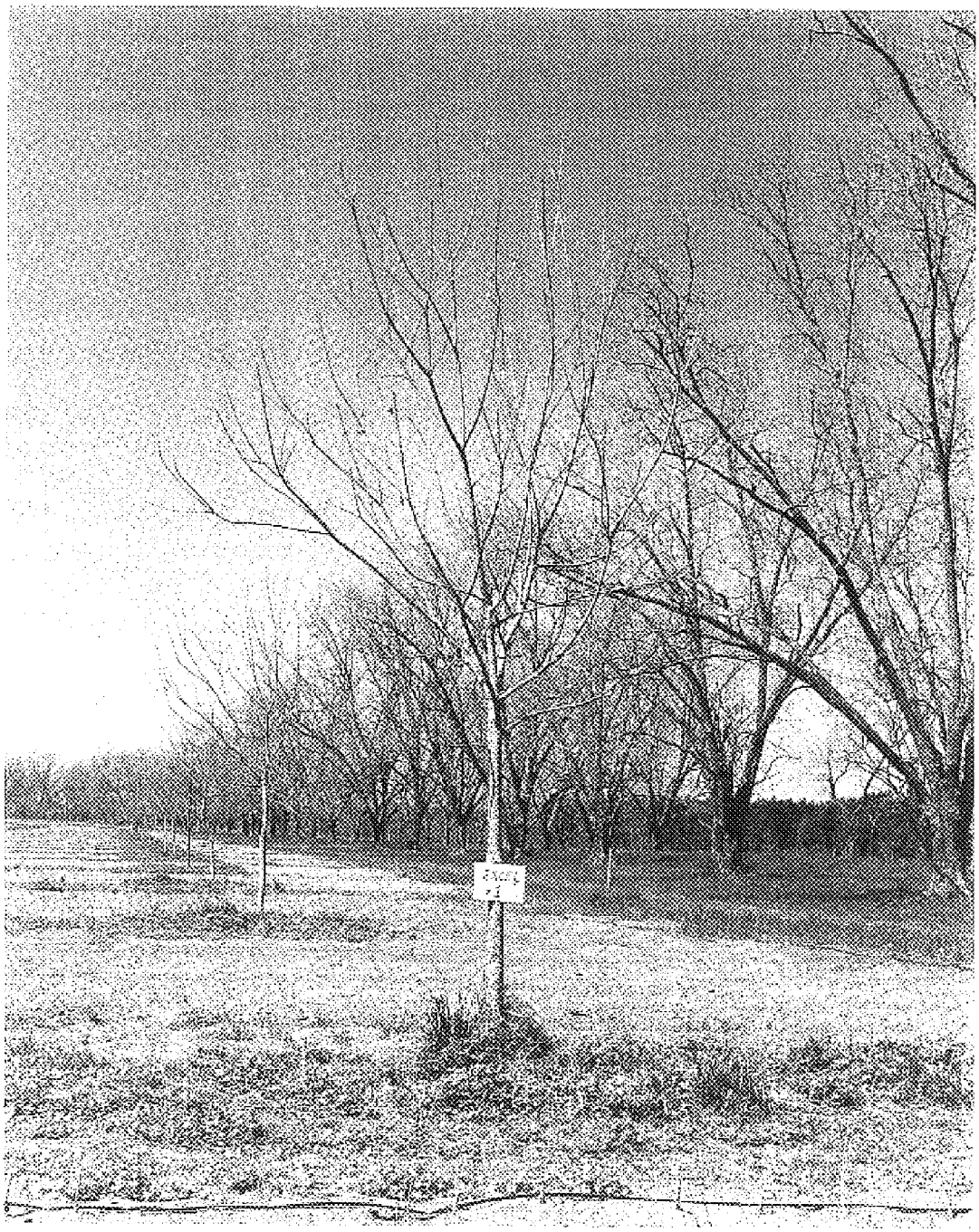
FIG. 7 illustrates the open growth of the branches of the new 'EXCEL' variety taken during the winter, while the tree is dormant.

The age of the tree exemplifying the present invention in FIGS. 1–7 is nine years.

The average plant height of the present invention is twenty feet. The average spread is twenty feet.

The following information describes the leafs and leaflets of the present invention.

Average leaf length: 37.5 cm.
Average leaflet length: 12.5 cm.
Average leaflet number: 11.
Average leaflet width: 3.5 cm.

The leaves or the present invention are odd pinnately compound with a variable number of leaflets. The typical leaflet is symmetrical, ovate-lanceoulate with an acute-attenuate apex and a decurrent base. Lateral leaflets are falcate, with the distal portion (toward the leaf apex) being convlex with an obtuse base. The proximal portion (toward the leaf base) is concave with an acute base. The apices of lateral leaflets are attenuate. Margins of all leaflets are serrate, except on the proximal sides of the lateral leaflet bases, which are entire. Venation is craspedodromous, with most of the secondary veins terminating at the leaflet margins, usually at the points of the serrations. The petiole and petiolules have slightly thickened bases. Petiolules are attached to the rachis so that the distal half of the leaflet is elevated above the plane of the rachis and also above the proximal half of the leaflet.

Average petiole length: 19.4 cm.
Average petiole diameter: 2 mm.
Petiole surface texture: Lightly Fuzzy.

The terminal winter buds of the present invention are about 12 mm long, acute, somewhat 4-angled, valvate, dark yellowish brown and scurfy. The lateral buds are similar but approximately 8 mm long, sharp pointed and covered by hairy scales.

The surface texture of the branches and twigs of the present invention are moderately stout, grayish-brown, hairy when immature but soon becoming smooth and have large 3-lobed leaf scars. The trunk surface texture (bark) is light brownish gray, divided into interlacing scaly ridges separated by narrow fissures.

The surface texture of the branches and twigs of the present invention are moderately stout, grayish-brown, hairy when immature but soon becoming smooth and have large 3-lobed leaf scars. The trunk surface texture (bark) is light brownish gray, divided into interlacing scaly ridges separated by narrow fissures.

The lenticels on the twigs of the present invention are irregular oval shaped, 1–2 mm in length, and grayish-orange in color. Lenticels on the trunk and branch are not observable.

The staminate catkins of the present invention are approximately 15 cm in length, slightly hairy, sessile, in 3-branched aments, and produced near the ends of the previous seasons' growth.

Catkin length: 13 cm.
Catkin diameter: 6 mm.
Number of stamens: 6.

The pistillate flowers are oblong, somewhat 4-angled, and yellowish scurfy.

Spike size: 2.5 cm.
Number of flowers per spike: 4 to 7.

Pollen is shed late in the pollination season and stigmas are receptive in the middle of the pollination season, which indicates that the 'Excel' pecan of the present invention is protogynous.

First female bloom: May 5.
Last female bloom: May 18.
First male bloom: May 1.
First female bloom: May 21.

The 'Excel' pecan of the present invention has been found to be resistant in the pecan scab disease caused by the fungus *Cladosporium caryigenum* (Ell. Et Lang.) Gottwald (1982).

The nut husk of the present invention is oblong, approximately 6 cm long and 3.5 cm wide. These husks are 4-angled and approximately 7 mm thick, with a surface texture which is smooth and non-hairy.

The 'Excel' pecan of the present invention is oblong in shape, with as stated smooth surface texture. The nut base shape is cuspidate and the nut apex is also cuspidate. The nuts have dark brown striping at the apex. The kernel shape is oblong to oval with prominent dorsal grooves running from the embryo to the cotyledon apex. The cotyledon edges have a prominent scalloped edging.

The kernels of the present invention (both cotyledons together) average approximately 4.5 grams. The kernel flavor is moderately sweet with a typical pecan oil flavor and a slight astringency. The kernels are very firm and crisp, but hold together well upon cracking and shelling. The average percentage kernel by weight is 51%, and the average percentage that shell into clean halves is 80%. The number of nuts per pound is 45. As stated, the kernel shape is oblong to oval with prominent dorsal grooves running from the embryo to the cotyledon apex. Also as stated, the cotyledon edges have a prominent scalloped edging.

DNA has been run on the 'EXCEL' variety and it was shown to be both unique and dissimilar to any other known variety. Limbs grow in an upright position but to be willowy when heavily laden with nuts which tends to reduce excessive limb breakage. Because of the nut size and thickness of the shell the nut is bird resistant. This tree has been grafted and reproduced extensively on the farm of origin and the offspring has shown to be very consistent to the parent tree.

Because of its large size attractive shape, high quality meat kernel and early maturity, the new 'EXCEL' variety should be an excellent choice for the in shell market as well as a good selection for commercial sellers.

What is claimed is:

1. A new and distinct variety of pecan tree substantially as shown and described herein, the new variety having a sturdy upright sparse tube showing small leaves and twig bits having a semi-dwarf type growth, the new variety being disease and insect resistant with excellent hardiness exhibiting a later bloom that the Stuart variety and an earlier maturing fruit, maturing about 14 days earlier than the Stuart variety, the fruit being of excellent kernel quality with bright meat and a heavy oil content.

* * * * *